(12) United States Patent
Yang

(10) Patent No.: US 7,309,414 B2
(45) Date of Patent: Dec. 18, 2007

(54) METHOD FOR MEASURING LOCALIZED CORROSION RATE WITH A MULTI-ELECTRODE ARRAY SENSOR

(75) Inventor: Lietai Yang, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 11/102,106

(22) Filed: Apr. 8, 2005

(65) Prior Publication Data
US 2005/0274628 A1 Dec. 15, 2005

Related U.S. Application Data

(60) Provisional application No. 60/560,858, filed on Apr. 9, 2004.

(51) Int. Cl.
*G01N 17/04* (2006.01)
(52) U.S. Cl. ............... 205/775.5; 204/404; 204/412; 324/693; 324/700; 324/71.1
(58) Field of Classification Search ..... 205/775.5–777; 204/404, 412; 324/700, 693, 71.1
See application file for complete search history.

(56) References Cited

U.S. PATENT DOCUMENTS

| | | | | |
|---|---|---|---|---|
| 3,331,021 A | 7/1967 | Marsh et al. | ............... | 205/775 |
| 3,924,175 A | 12/1975 | Wilson | ............... | 324/30 R |
| 4,158,806 A | 6/1979 | Kotylev et al. | ............... | 324/65 R |
| 4,351,703 A * | 9/1982 | Winslow, Jr. | ............... | 205/724 |
| 4,717,673 A | 1/1988 | Wrighton et al. | ............... | 436/68 |
| 4,840,719 A | 6/1989 | Jasinski | ............... | 204/404 |
| 4,874,500 A | 10/1989 | Madou et al. | ............... | 204/412 |
| 5,015,355 A | 5/1991 | Schiessl | ............... | 204/404 |
| 5,139,627 A | 8/1992 | Eden et al. | ............... | 205/775.5 |
| 5,306,414 A | 4/1994 | Glass et al. | ............... | 204/404 |
| 6,132,593 A * | 10/2000 | Tan | ............... | 205/776.5 |
| 6,683,463 B2 | 1/2004 | Yang et al. | ............... | 324/700 |
| 2002/0153907 A1* | 10/2002 | Yang et al. | ............... | 324/700 |

OTHER PUBLICATIONS

International PCT Search Report and Notification of Receipt of Demand PCT/US02/09608, 8 pages, Nov. 15, 2002.

Lumsden, J.B., et al.; "Electrochemical Noise for Carbon Steel in Sodium Chloride Solutions-Effect of Chloride and Oxygen Activity", Corrosion 92, Paper N0 224, The NACE Annual Conference, Houston, TX, 1992.

Qingdong, Z.; "A Novel Electrochemical Testing Method and Its Use in the Investigation of Underfilm Corrosion of Temporary Protective Oil Coating", Corrosion, vol. 56, No. 7; pp. 722-725, Jul. 2000.

Rothwell, A.N., et al.; "Electrochemical Noise Techniques for Determining Corrosion Rates and Mechanisms", Corrosion 92, Paper N0 223, The NACE Annual Conference, Houston, TX, 9 pages, 1992.

(Continued)

*Primary Examiner*—Nam Nguyen
*Assistant Examiner*—Surekha Vathyam
(74) *Attorney, Agent, or Firm*—Baker Botts L.L.P.

(57) ABSTRACT

A method of measuring localized corrosion, using a multi-electrode array sensor. The method eliminates the effect of internal current in corroded electrodes, and thus provides a more accurate corrosion measurement. In one embodiment, the potential of a common node of the sensor is adjusted so that the sensor's most cathodic current is close to zero.

5 Claims, 3 Drawing Sheets

OTHER PUBLICATIONS

Sikora, J., et al.; "Analysis Current and Potential Oscillations on 304 SS During Metalstable Pitting", Proceedings of the Symposium on Critical Factors in Localized Corrosion III; The Electrochemical Society, Inc., Pennington, NJ; pp. 508-518, 1999.

Steinsmo et al., "Aspects of testing and selecting stainless steels for sea water applications" 1994, Paper #492, Corrosion 94, Annual Conference of Corrosion show Sponsored by NACE International, 18 pages, 1994.

Fei, Z. et al., "Spatiotemporal Patterns on Electrode Arrays", J. Phys. Chem., vol. 100, No. 49, pp. 18986-18991, 1996.

PCT International Search Report, PCT/US04/09107, 16 pgs, Mailing Date Jun. 3, 2005.

PCT International Search Report, PCT/US05/12155, 8 pages, Nov. 8, 2006.

PCT International Preliminary Report of Patentability, 7 pages, Apr. 5, 2007.

* cited by examiner

METHOD FOR MEASURING LOCALIZED CORROSION RATE WITH A MULTI-ELECTRODE ARRAY SENSOR

RELATED PATENT APPLICATION

This application claims the benefit of U.S. Provisional Application No. 60/560,858, filed Apr. 9, 2004 by Lietai Yang and entitled "Improved Method for Measuring Localized Corrosion Rate with a Multi-Electrode Array Sensor".

TECHNICAL FIELD OF THE INVENTION

This invention relates to methods for detecting corrosion in metals, and more particularly methods for using a sensor having an array of electrochemical cells.

BACKGROUND OF THE INVENTION

Corrosion is a natural process that involves a metal atom M being oxidized, whereby it loses one or more electrons and leaves the bulk metal, $M \rightarrow M^{m+} + m\ e^-$. The lost electrons are conducted through the bulk metal to another site where they reduce (i.e. combine with) a reducible species such as a dissolved gas or a positively charged ion $G^+$ that is in contact with the bulk metal, $N + n\ e^- \rightarrow N^{n-}$ and $G^{m+} + m\ e^- \rightarrow G$.

In corrosion parlance, the site where metal atoms lose electrons is called the anode, and the site where electrons are transferred to the reducible species is called the cathode. These sites can be located-close to each other on the metal's surface, or far apart depending on the circumstances. When the anodic and cathodic sites are continuous, the corrosion is more or less uniform across the surface. When these sites are far apart, the anodic sites corrode locally.

A corrosion path is essentially an electric circuit, since there is a flow of current between the cathode and anode sites. In order for a current to flow, Kirchoff's circuit laws require that a circuit be closed and that there exists a driving potential (or voltage). Part of the corrosion circuit is the base metal itself; the rest of the circuit exists in an external conductive solution (i.e. an electrolyte) that must be in contact with the metal. This electrolyte serves to take away the oxidized metal ions from the anode and provide reduction species (either nonmetalic atoms or metallic ions) to the cathode. Both the cathode and anode sites are immersed in an electrolyte for the corrosion circuit to be complete.

In corroding systems, potential gradients can be created by a number of mechanisms. These include differences in the free energy or the related electrochemical potentials for different reactions and gradients in the concentration of charged species in the solution. When two electrodes exhibiting differing potentials are electrically connected, a current flows in the external circuit.

Corrosion can be measured by attaching a sensor directly to an area on a component of interest. When it is not practical to directly test the component of interest itself, separate sensors can be installed in the same environment. These sensors test a sample of the same material as the component of interest and can be removed from the main component structure and examined in detail. The use of such sensors facilitates the measurement of corrosion damage in a well-controlled manner over a finite sensor area.

There are various approaches to monitoring corrosion; electrochemical approaches rely on the above-described electrochemical corrosion principles and the measurement of potentials or currents to monitor corrosion damage.

One approach to monitoring corrosion is an electrical noise method, which uses electrodes to detect electrochemical noise due to localized corrosion. This method has been implemented using a single pair of near identical large electrodes, and measuring the current noise between the two electrodes. With two large electrodes, each may have a number of anodic areas and a number of cathodic areas, resulting in the possibility of zero current flows between the two electrodes. In general, the overall current noise method is not well suited to indicating corrosion rate at a particular site of the metal.

U.S. Pat. No. 6,132,593 to Tan, entitled "Method and Apparatus for Measuring Localized Corrosion and Other Heterogeneous Electrochemical Processes", describes one example of a multi-electrode sensor that may be used to simulate a one-piece electrode. Another example of a multi-electrode sensor is described in U.S. Pat. No. 6,683,463 to Yang and Sridhar, entitled "Sensor Array for Electrochemical Corrosion Monitoring".

DETAILED DESCRIPTION OF THE INVENTION

Overview

As stated in the Background, U.S. Patent Nos. 6,132,593 and No. 6,683,463 each describe types of multi-electrode array sensors for monitoring localized corrosion. In particular, the latter array has been tested extensively using carbon steels, stainless steels, and nickel-base alloys as probe elements in cooling water, simulated sea water with sulfate reducing bacteria, under salt deposits, concentrated chloride solutions, and a process stream of a chemical plant. It has been demonstrated that the sensor is highly sensitive to the corrosiveness of the environments for localized corrosion.

Quantitative prediction of the penetration rate of localized corrosion involves the assumption that there is no current that flows internally on the most corroded electrode. This assumption may be true or close to reality if the environment is highly corrosive and some of the sensor electrodes are severely corroded. However, for a less corrosive environment, or during the early stages of corrosion when no electrode is more significantly corroded than the others in the sensor, this assumption may not be valid and therefore the predicted results may underestimate the true corrosion penetration rate.

The following description is directed to a method that may be used to eliminate or reduce the internal current. As a result, the measured corrosion penetration rate is closer to the true corrosion rate that takes place on the most anodic electrode in the sensor.

Multi-Electrode Array Sensors

For purposes of example, the method described herein is described in terms of use with the multi-electrode sensor array of U.S. Pat. No. 6,683,463, including its various embodiments. That patent is incorporated by reference herein. However, the same method could be used with other multi-electrode array sensors used for corrosion monitoring. By "multi-electrode array sensor" is meant any corrosion sensor having multiple electrodes that may be used to simulate a one-piece electrode at a corrosion site of interest.

Figure 1:
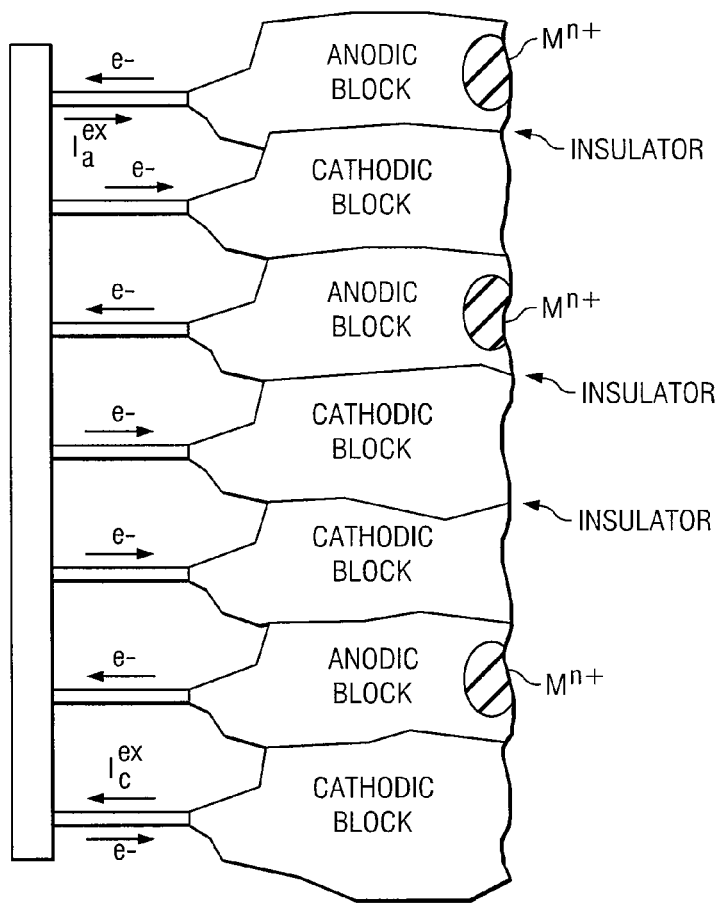
FIG. 1 illustrates the principle of a coupled multi-electrode array sensor

FIG. 1 illustrates the working principle of a coupled multi-electrode array sensor. Electrically insulating pieces of the surface area permit the electron flow from each anodic area or into each cathodic area to be measured. In principle, the metal is divided into an array of small blocks separated from each other by an insulator and connected together externally. The result is an array of identical blocks that are prevented from touching each other directly, but are connected externally to simulate a larger piece of metal. Each block may be cathodic or anodic depending on its corrosion. For each block, the integration of current, I, flowing into a given anodic area, $I_a$, or from a cathodic area, $I_c$, over a period of time is related to the extent of growth of local corrosion at the surface of the block.

The corrosion currents that flow through the external circuit from the less corroding or non-corroding electrodes (or cathodic electrodes) to the more corroding (or more anodic electrodes) are used to measure the localized corrosion rate. The total anodic current on the most corroded electrode corresponds to the highest corrosion rate or maximum penetration rate on the sensor.

Figure 2:
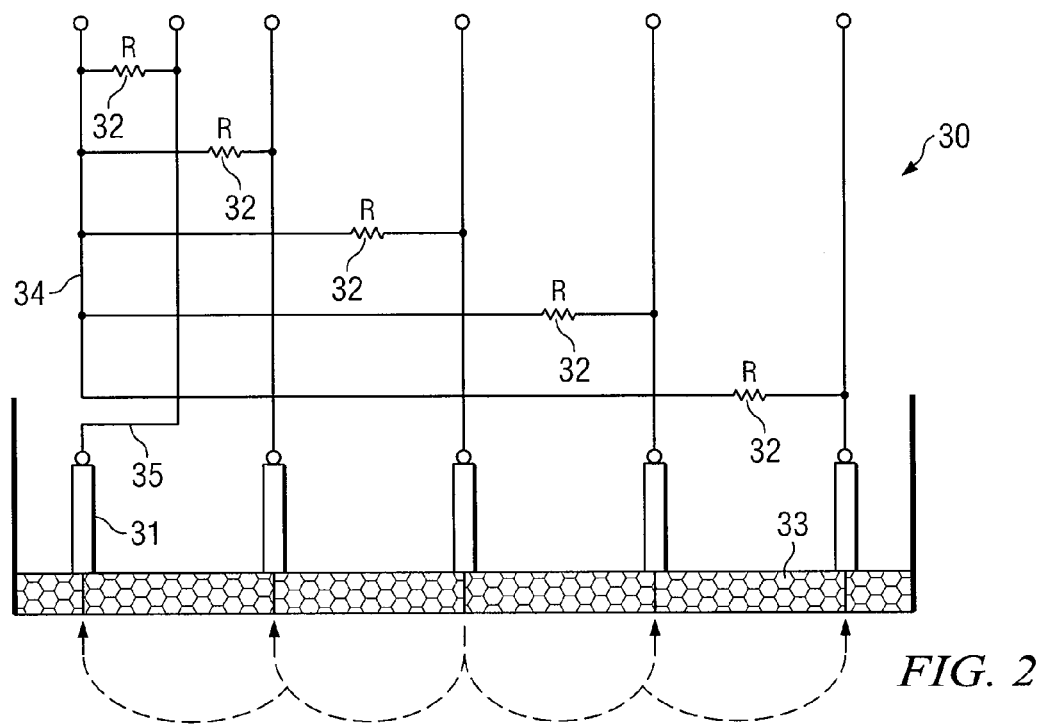
FIG. 2 is a representative drawing of a coupled multi-electrode sensor, with which the method of the invention may be implemented.

FIG. 2 is a representative drawing of a multi-electrode sensor 30. Each of the blocks of FIG. 1 is replaced by an electrode 31 made from the same material as a metal of interest. Each electrode 31 is a small piece of material or a wire, with a small surface area exposed to the electrolyte at the bottom surface of a base 33. The electrodes 31 are supported as a solid array by a solid insulating material between them, which forms an insulating base 33. An example of a suitable insulating material is an epoxy. Other insulating materials may be used as determined by environmental conditions, such as temperature and pressure.

Above the insulating base 33, each electrode 31 is connected to an electrical lead 35. As illustrated, portions of each electrode 31 encapsulated in the base 33 may be made thicker or thinner than portions outside base 33, depending on considerations such as durability, handling convenience, or fabrication.

A small resistor 32 is connected between each electrode 31 and a common electrical connection 34. The current flowing into or from each electrode can be measured by the voltage drop across the resistor 32. Each electrode output is delivered to a channel input of a voltmeter (not shown), and the voltage measurements are used to calculate current.

During experimentation using sensor 30, it was observed that crevices may form to some degree between the epoxy and metal at some of the electrodes 31. These crevices can introduce undesired additional corrosion at their sites. To minimize the formation of these crevices, sputtering or passivation methods may be used to form an inert film on the side surface of the electrode 31 before epoxy is applied.

Sensor 30 can also be implemented without a solid base 33. Various alternative means of supporting the array of electrodes 31 could be devised. For example, the electrodes 31 could be attached to each other in a grid like fashion, with supporting branches of insulating material between them.

In operation, sensor 30, whose electrodes 31 are made from the same material as a structure of interest, may be placed in the same environment as the structure of interest. Sensor 30 may then be used to monitor corrosion of electrodes 31, thereby indicating corrosion of the structure of interest. For example, to monitor corrosion within a pipeline, electrodes 31 are made from the same material as the inner surface of the pipeline and sensor 30 is inserted as a probe into the pipeline.

When a large number of electrodes 31 are used, some of the electrodes 31 may exhibit more anodic or cathodic properties than others. The differences in electrochemical response of these electrodes will differ depending on the corrosivity of the environment. For example, in a saline solution that causes localized corrosion, the presence of certain inclusions in the metal will cause very anodic behavior. However, these same inclusions will not cause such an anodic response in another more benign solution.

A feature of the sensor 30 is that rather than measuring current between pairs of electrodes, the current is measured between each electrode 31 and all other electrodes 32 of the same metal. This simulates the localized corrosion processes occurring at different sites of the metal when sensor 30 is placed in a corrosion environment.

By addressing each electrode 31 in a rectangular or circular grid successively through electrical means and tracking their locations, spatial variation in localized corrosion can be tracked. This eliminates the need for mechanical scanning devices, which are needed in the case of a single electrode.

The anodic current into each corroding electrode 31 is directly proportional to the corrosion rate at that site. This may be expressed as follows:

$$\text{Corrosion Rate} = \text{Corroding Area Factor} \times \text{Conversion Factor} \times \text{Anodic Current Density}$$

For pitting type corrosion, The Corroding Area Factor may be estimated from the ratio of the area of the total pits to the area of the total electrode surface.

Sensor 30 measures averaged DC current flowing into specific corrosion sites. It is thus able to detect a corrosion rate at specific sites of a metal. The coupling of a large number of electrodes 31 guarantees that there are always some electrodes 31 representing corrosion sites of a metal in a corrosion environment.

In experimentation, sensor 30 was implemented with 25 electrodes 31, in a 5×5 array. Electrodes 31 were made from stainless steel 304 wire. Sensor 30 was placed in de-ionized water, and analysis was made of the currents of the 25 electrodes 31 and the responses of the current signals to the changes in the solution chemistry. Simple parameters such as 5 percentile anodic currents or the standard deviation among the 25 electrodes were useful as effective localized corrosion indicators.

Derivation of the corrosion rate on the basis of the variance of the currents allows the use of a single parameter (standard deviation or nth percentile anodic current) to represent localized corrosion rate. This greatly simplifies the method so that a plant or field operator having only limited knowledge of corrosion may easily understand the signal from the sensor.

Improved Method for Measuring Corrosion

An improved method of using a multi-electrode sensor, such as sensor 30, is based on the recognition of an internal flow of electrons within electrodes of the sensor. In effect, the method removes the effect of this internal flow.

Figure 3A:
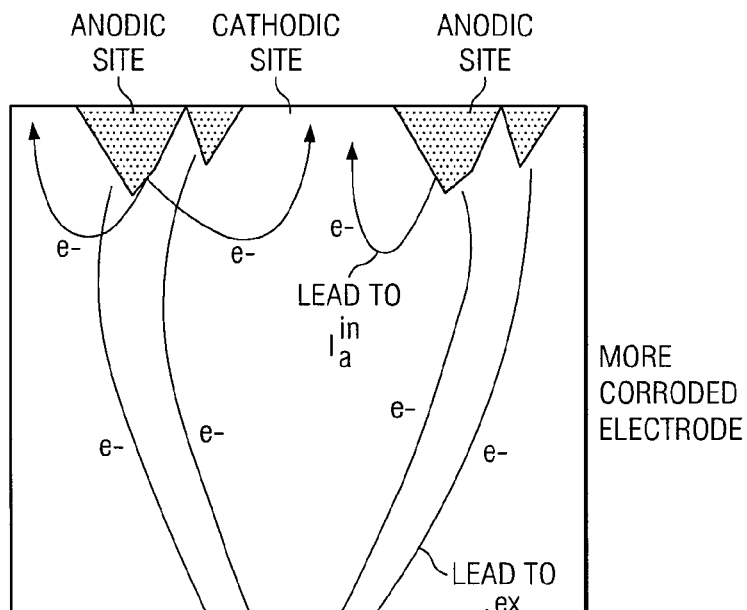
FIGS. 3A and 3B illustrate the electron flow pattern within anodic and cathodic electrodes, respectively.
Figure 3B:
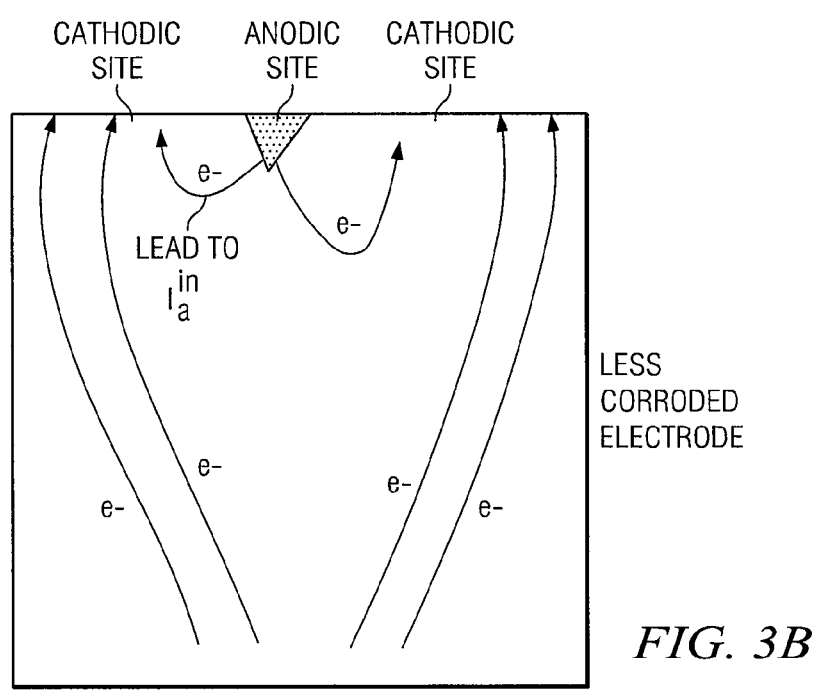

FIGS. 3A and 3B illustrate the flow pattern of electrons from anodic sites to both internal (own electrode) and external (other electrode) cathodic sites in a coupled multi-electrode sensor. FIG. 3A illustrates the flow pattern of a more corroded electrode, whereas FIG. 3B illustrates the flow pattern of a less corroded electrode.

As indicated in FIGS. 3A and 3B, the total anodic current, $I_a$, is the sum of the external anodic current, $I_a^{ex}$, and the internal anodic current that flows from the cathodic sites within the electrode, $I_a^{in}$:

$$I_a = I_a^{ex} + I_a^{in} \quad (1)$$

The coupled multiple-electrode sensor relies on the measurement of the external anodic current to estimate the corrosion rate according to Equation (1). As $I_a^{in}$ is not measurable, the corrosion current may also be expressed as:

$$I_a = I_a^{ex}/\epsilon \quad (2)$$

, where $\epsilon$ is a current distribution factor, ranging from 0 to 1, that represents the fraction of electrons that flow to other electrodes through the external circuit. If an electrode is more corroded than most of the other electrodes of the sensor, most of its corrosion electrons would flow to the other electrodes through the external circuit, and its $\epsilon$ would be close to unity. On the other hand, if an electrode is less corroded, most or all of its corrosion electrons would flow to the local cathodic sites, and its $\epsilon$ would be close to or equal to zero.

The reason for the existence of the internal current for the most corroded electrode is that there are cathodic sites available on the most anodic electrode, i.e., the potential of the cathodic sites, if they can be isolated and measured, are higher than the effective potential of the most corroded electrode. This is so-even though the potential of the most corroded electrode is already elevated from its averaged open circuit potential by coupling it to the other electrodes.

If the potential of the most corroded electrode is raised and maintained at a special value, Es, that is equal to or slightly more positive than the potential of the most cathodic site on the electrode, the internal current would be eliminated. The question is how to determine this Es.

One approach to eliminate internal current is to equate $E_s$ to the potential of the most cathodic electrode (the electrode that has the highest open circuit potential if decoupled). This is because each electrode in the coupled multi-electrode array sensor simulates either an anodic or a cathodic site for the collection of the electrodes. In other words, all the electrodes are connected to behave as one piece of metal. Thus, the most cathodic electrode simulates the most cathodic site on the metal.

In practice, this may be achieved by adjusting the potential of the common joint of a coupled multi-electrode array sensor such that the sensor's most cathodic current is close to zero. This potential is the Es. If no current is cathodic, the open circuit potentials of all the electrodes are lower than the potential of the coupling joint. This is equivalent to the case when no internal cathodic current exists on the most corroded electrode. Therefore, the current distribution factor $\epsilon=1$, and $$I_{corr} = I_a^{ex} \quad (3)$$

. It should be mentioned that the potential should not be too far from Es. If the potential is too low, the internal current cannot be eliminated; if the potential is too high, the sensor is adversely polarized.

Figure 4:
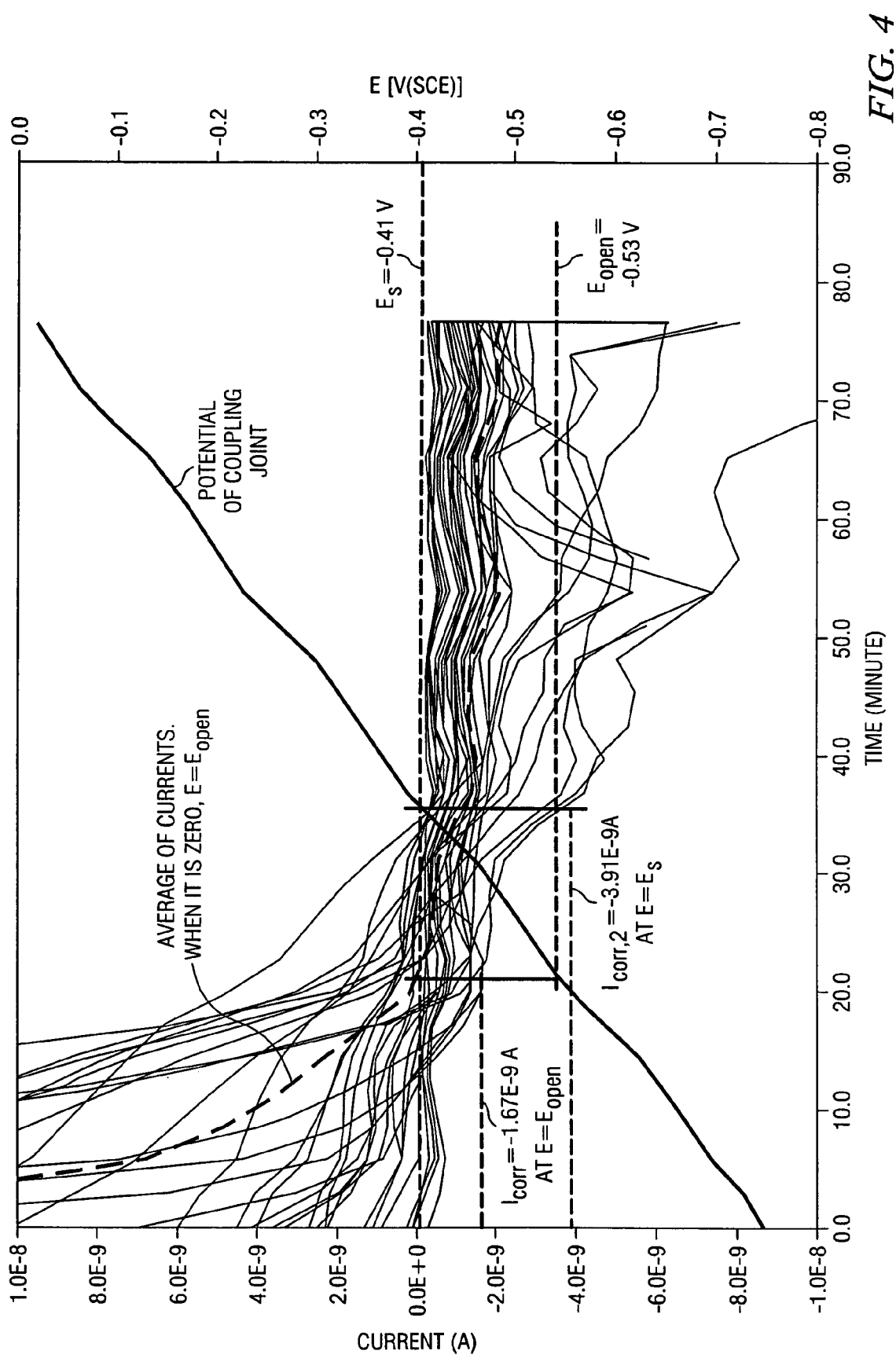
FIG. 4 illustrates results of experimentation, using the method of the invention.

FIG. 4 illustrates partial results from an early cyclic voltammetry experiment with Type 302 stainless steel in 0.5 M NaCl at room temperature. More, specifically it illustrates sensor currents during a segment of cyclic potentiodynamic polarization. $I_{corr}$ is the maximum anodic external current at open circuit potential and is used to estimate the corrosion current in the previous method. $I_{corr,2}$ is the maximum anodic external current when the potential is controlled as $E_s$. $I_{corr,2}$ should be equal to the corrosion current because the internal current is zero under this condition.

The experiment of FIG. 4 demonstrates that the multi-electrode array sensor may be used to monitor the effectiveness of cathodic protection, i.e. to monitor localized corrosion when the sensor or the system to be protected is under polarization. When the sensor was at open circuit potential (the potential at which the average current is zero), some of the currents were anodic (negative in the figure) and some of the currents were cathodic (positive). This simulated the behavior of a piece of metal in an environment under natural corroding conditions.

When the coupling potential was at Es, the potential at which the last detectable cathodic current began to disappear and all the currents were anodic, the process simulated a case where no internal current in a metal existed and the corrosion currents equaled the maximum external anodic current (Equation 3). The corrosion current measured at Es is about twice of the external current measured at the open circuit potential, indicating that previously implemented measurement methods may underestimate the corrosion current by about 50%.

It should be mentioned that the above test was conducted in a continuous large-scale cyclic potential sweeping manner, and the current measurement may be somewhat distorted because of the kinetic effects. Additional measurement could be carried out under quasi-dynamic conditions. That is, the potential could be dynamically controlled near the Es value to further prove the concept.

OTHER EMBODIMENTS

Although the present invention has been described in detail, it should be understood that various changes, substitutions, and alterations can be made hereto without departing from the spirit and scope of the invention as defined by the appended claims.

What is claimed is:

1. A method of eliminating the effect of internal current in a multi-electrode array sensor at a corrosion site of interest, the sensor being capable of providing current measurement values from multiple electrodes, comprising:
   exposing the sensor to the corrosion at the site of interest;
   wherein the sensor has an array of substantially similar metallic electrodes arranged such that each electrode has a surface area operable to be exposed to the corrosion site, and such that each electrode is electrically insulated from other electrodes;
   wherein each electrode is operable as an anode or cathode depending on the extent of corrosion at that electrode;
   wherein each electrode is electrically connected to a common node, such that the sensor simulates a one-piece electrode surface;
   determining an electrical potential value, $E_s$, for the common node;
   wherein $E_s$ is substantially the minimum potential value at which the current measurement values from all electrodes are equal to or less than zero.

2. The method of claim 1, wherein the electrodes are each connected to the common node through a resistor.

3. The method of claim 1, wherein the determining step is performed by determining the voltage at the common node at which the current associated with the most cathodic electrode is substantially zero.

4. The method of claim 1, wherein the determining step is performed by incrementally raising the potential at the common node from open circuit potential to $E_s$, and measuring currents from the electrodes at each increment.

5. A method of eliminating the effect of internal current in a multi-electrode array sensor when measuring corrosion at a corrosion site of interest, the sensor being capable of providing current measurement values from multiple electrodes, comprising:

exposing the sensor to the corrosion at the site of interest;

wherein the sensor has an array of substantially similar metallic electrodes arranged such that each electrode has a surface area operable to be exposed to the corrosion site, and such that each electrode is electrically insulated from other electrodes;

wherein each electrode is operable as an anode or cathode depending on the extent of corrosion at that electrode;

wherein each electrode is electrically connected to a common node, such that the sensor simulates a one-piece electrode surface;

raising the potential at the common node from open circuit;

measuring currents from the electrodes;

repeating the raising and measuring steps to determine the minimum potential value at which the currents measure zero or less than zero; and applying the minimum potential value to the common node.

* * * * *